US012680060B2

(12) United States Patent　　　　(10) Patent No.:　US 12,680,060 B2

Kulkarni et al.　　　　　　　　　　(45) Date of Patent:　　Jul. 14, 2026

(54) INTEGRATED SYSTEM AND METHOD FOR METHANE PRODUCTION USING OFF GAS RECYCLING TO ANAEROBIC DIGESTER FROM A GAS SEPARATION MEMBRANE UNIT

(71) Applicant: L'Air Liquide, Societe Anonyme pour l'Etude et l'Exploitation des Procedes Georges Claude, Paris (FR)

(72) Inventors: Sudhir Kulkarni, Wilmington, DE (US); Min Ho Maeng, Newark, DE (US); Shu Fang, Newark, DE (US)

(73) Assignee: L'Air Liquide, Société Anonyme pour l'Etude et l'Exploitation des Procédés Georges Claude, Paris (FR)

( * ) Notice: Subject to any disclaimer, the term of this patent is extended or adjusted under 35 U.S.C. 154(b) by 743 days.

(21) Appl. No.: 17/961,310

(22) Filed: Oct. 6, 2022

(65) Prior Publication Data

US 2024/0117285 A1　　Apr. 11, 2024

(51) Int. Cl.
　　*C12M 1/107*　　(2006.01)
　　*B01D 53/00*　　(2006.01)
　　*C12M 1/00*　　(2006.01)
(52) U.S. Cl.
　　CPC ............ *C12M 21/04* (2013.01); *C12M 23/58* (2013.01); *C12M 29/04* (2013.01)
(58) Field of Classification Search
　　CPC ...... C12M 21/04; C12M 23/58; C12M 29/04; C10L 3/104; C10L 2290/02; C10L 2290/10; C10L 2290/26; C10L 2290/46; C10L 2290/548; B01D 2256/245; B01D 2257/504; B01D 2258/05; B01D 53/227; B01D 53/22
See application file for complete search history.

(56) References Cited

U.S. PATENT DOCUMENTS

| | | | |
|---|---|---|---|
| 7,025,803 B2 | 4/2006 | Wascheck et al. | |
| 8,409,439 B1 | 4/2013 | Tovani et al. | |
| 9,988,326 B2 | 6/2018 | Paget et al. | |
| 10,179,883 B2 | 1/2019 | Mitariten | |
| 10,589,215 B2 | 3/2020 | Ding et al. | |
| 2002/0079266 A1 | 6/2002 | Ainsworth et al. | |
| 2012/0118011 A1 | 5/2012 | Terrien et al. | |
| 2016/0184769 A1* | 6/2016 | Kulkarni ............ | C01B 23/0042 |
| | | | 95/45 |

(Continued)

FOREIGN PATENT DOCUMENTS

| | | |
|---|---|---|
| CN | 104003832 | 8/2014 |
| CN | 104651412 | 5/2015 |

(Continued)

OTHER PUBLICATIONS

English language machine translation of WO2015155427A1, 14 pages, No Date.*

(Continued)

*Primary Examiner* — Pranav N Patel

(74) *Attorney, Agent, or Firm* — Yan Jiang; Christopher J. Cronin

(57)　　　　ABSTRACT

Raw biogas from an anaerobic digester is fed to a membrane separation unit that produces methane rich biomethane and a CO2 rich permeate that is recycled to the anaerobic digester where it is mixed with the digestate.

17 Claims, 6 Drawing Sheets

(56)                    References Cited

U.S. PATENT DOCUMENTS

| | | | |
|---|---|---|---|
| 2018/0251694 A1 | 9/2018 | Foody et al. | |
| 2019/0024617 A1 | 1/2019 | Fukui et al. | |
| 2019/0030482 A1 | 1/2019 | Ding et al. | |
| 2020/0177787 A1 | 6/2020 | Satou et al. | |
| 2020/0188843 A1 | 6/2020 | Barraud et al. | |
| 2020/0254383 A1 | 8/2020 | Roodbeen | |
| 2021/0339189 A1* | 11/2021 | Winkler | B01D 53/0423 |
| 2022/0203293 A1 | 6/2022 | Myrick | |
| 2022/0203294 A1 | 6/2022 | Myrick | |

FOREIGN PATENT DOCUMENTS

| | | |
|---|---|---|
| CN | 108624370 | 10/2018 |
| EP | 2 614 890 | 7/2013 |
| EP | 3 964 558 | 3/2022 |
| FR | 3048366 | 9/2017 |
| KR | 2012 0119755 | 10/2012 |
| KR | 101327338 | 11/2013 |
| KR | 101509133 | 4/2015 |
| KR | 2017 0123726 | 11/2017 |
| KR | 2019 0009966 | 1/2019 |
| WO | WO 2015 155427 | 10/2015 |
| WO | WO 2022 012944 | 1/2022 |
| WO | WO 2023 2212754 | 11/2023 |

OTHER PUBLICATIONS

Alibardi, L. et al., Performance and stability of sewage sludge digestion under $CO_2$ enrichment: a pilot study, Bioresource Technology 245 (2017) 581-589.

Al-Mashhadani, M.K.H. et al., Carbon dioxide rich microbubble acceleration of biogas production in anaerobic digestion, Chemical Engineering Science 156 (2016) 24-35.

Angelidaki, I. et al., Biogas upgrading and utilization: current status and perspectives, Biotechnology Advances 36 (2018) 452-466.

Bajon Fernandez, Y. et al., Carbon capture and biogas enhancement by carbon dioxide enrichment of anaerobic digesters treating sewage sludge or food waste, Bioresource Technology 159 (2014) 1-7.

Bajon Fernandez, Y. Enhancing the anaerobic digestion process through carbon dioxide enrichment: initial insights into mechanisms of utilization, Enviromental Technology 2019, vol. 40, No. 13, 17844-1755.

Bakonyi, P. et al., A novel gas separation integrated membrane bioreactor to evaluate the impact of self-generated biogas recycling on continuous hydrogen fermentation, Applied Energy 190 (2017) 813-823.

Bergamo, U. et al., Analysis of anaerobic digester mixing: comparison of long shafted paddle mixing vs gas mixing, Water Science & Technology, 81.7, 2020, 1406-1419.

Esposito, E. et al., Simultaneous production of biomethane and food grade $CO_2$ from biogas: an industrial case study, Energy Environ. Sci. 2019, 12, 281-289.

Koch, K. et al., Methane from $CO_2$: influence of different $CO_2$ concentrations in the flush gas on the methane production in BMP tests, Waste Management 49 (2016) 36-39.

Kovalev, A.A. et al., Feasibility study of anaerobic codigestion of municipal organic waste in moderately pressurized digesters: a case for the Russian Federation, Applied Sciences 2022, 12, 2933, 1-14.

Lee, D.-Y. et al., Effect of organic loading rate on continuous hydrogen production from food waste in submerged anaerobic membrane bioreactor, Int'l Journal of Hydrogen Energy 39 (2014) 16863-16871.

Lee, J.C. et al., Biological conversion of $CO_2$ to $CH_4$ using hydrogenotrophic methanogen in a fixed bed reactor, J. Chem Technol Biotechnol 2012; 87: 844-847.

Lemmer, A. et al., Integration of a water scrubbing technique and two-stage pressurized anaerobic digestion in one process, Energies (2015) 8 2048-2065.

Lindeboom, R.E.F., Autogenarative high pressure digestion: biogas production and upgrading in a single step, Water Science & Technology (2011) 64(3) 647-653.

Muntau, M. et al., Effects of $CO_2$ enrichment on the anaerobic digestion of sewage sludge in continuously operated fermenters, Bioresource Technology 332 (2021) 125147, 1-10.

Ramirez-Morales, J.E. et al., Evaluation of two gas membrane modules for fermentative hydrogen separation, Int'l Journal of Hydrogen Energy 38 (2013) 14042-14052.

Salomoni, C. et al., Enhanced methane production in a two-phase anaerobic digestion plant, after $CO_2$ capture and addition to organic wastes, Bioresource Technology 102 (2011) 6433-6448.

Siciliano, A. et al., Performance evaluation of pressurized anaerobic digestion (PDA) of raw compost leachate, Fermentation 2022, 8, 15, 1-17.

Singh, B. et al., State of the art on mixing in an anaerobic digester: a review, Renewable Energy 141 (2019) 922-936.

Statistical Report of the European Biogas Association 2021, Brussels, Belgium, Nov. 2021, 140 pages.

European Search Report and Written Opinion for related EP 23201634, Feb. 15, 2024.

* cited by examiner

INTEGRATED SYSTEM AND METHOD FOR METHANE PRODUCTION USING OFF GAS RECYCLING TO ANAEROBIC DIGESTER FROM A GAS SEPARATION MEMBRANE UNIT

CROSS-REFERENCE TO RELATED APPLICATIONS

None.

BACKGROUND

Field of the Invention

The present invention relates to the purification of digester gas.

Related Art $CO_2$ plays a role within digester microbial processes.

Several researchers have shown that exogenous $CO_2$ (i.e., $CO_2$ that is produced external to the digestion process) can be injected into various types of anaerobic digesters resulting in increased $CH_4$ production. These publications do not describe the purification of the biogas stream product of the digestion and do not recycle the product biogas in any form back to the digester.

Various upgrading processes based on adsorption, water scrubbing or membranes are available for the purification of raw biogas produced by landfills, digesters, or waste water treatment for providing renewable natural gas (RNG). The current state of art is a two or more stage membrane process which removes acid gases such as $CO_2$ from the RNG. The feed gas is typically filtered, treated for removal of contaminants such as $H_2S$, polar and heavy organics, and then compressed, typically to 10-15 bar. The compressed cleaned gas is then fed to one or more membrane stages where $CO_2$ preferentially permeates into the lower pressure permeate gas typically at a pressure of 1-2 bar. The CH4 enriched in the residue to a concentration of 95+ vol. % is typically polished further as needed and then compressed by a booster for injection into a natural gas pipeline.

Previous schemes do not recycle the $CO_2$ enriched permeate stream to the digester but utilize such streams in other beneficial ways, such as production of liquid $CO_2$ and inerting the ullage of tanks.

Several in the patent literature have proposed purification processes for raw biogas but not recycling of the $CO_2$ therefrom back to an anaerobic digester that produces the raw biogas.

U.S. Pat. No. 7,025,803 discloses a biogas membrane purification process for producing a $CH_4$ enriched biomethane product and a $CO_2$ enriched permeate in which the permeate from the 1st stage is used to regenerate adsorbent beds in an upstream PSA and the permeate from the 2nd stage is recycled to the compressor suction to reduce hydrocarbon losses. Similar schemes include U.S. Pat. No. 9,988,326 and US 2019/224617 A.

KR101327338 discloses a method of methane production and carbon dioxide recovery. A temperature control step provides feed biogas with heat energy to have the optimum incoming temperature for membrane separation. After $CO_2$ liquefaction, remaining methane is used as combustion source for the temperature control step (energy saving). A first membrane step (feed pressure 10-20 bar) does bulk removal of the $CO_2$ which preferentially permeates through the membrane. A second membrane step separates remaining $CO_2$ for more than 99% purity methane. A third membrane separation step separates and concentrates the remaining methane. The concentrated methane returns to compressed biogas stream after a compression unit. and results in 99% purity $CO_2$. Activated carbon is used for gas phase desulfurization and cooling water heat exchanger (T=4° C.) is used for moisture condensation/removal.

KR101509133 discloses the usage of a two-stage membrane system for high recovery of biogas. $CO_2$ in the raw biomethane is converted to $CaCO_3$ by adding $CaO+H_2O$ or $Ca(OH)_2$, thus resulting in reduced greenhouse gas (GHG) emissions. Membrane pressure is maintained at max 2 bar and more than 97% purity $CH_4$ is recovered. The patent does not teach recycle of $CO_2$ to the biogas production step (anaerobic digester).

KR101986776 discloses a method for refining biogas via adsorption-membrane separating process. Pressurized biogas is sent to adsorption unit for $CO_2$ adsorption and $CH_4$ recovery. The adsorbed $CO_2$ is desorbed and sent to the membrane separation unit. When feed biogas is overloaded and the recovery efficiency of $CH_4$ is reduced in the adsorption unit, a membrane separation unit additionally recovers $CH_4$ from desorbed gas. Recovered $CH_4$ from the membrane separation unit is recirculated back to the feed stream before a compression unit. A pressure reducing device after membrane uses pressure of −0.5 to −0.95 bar and the membrane permeability for $CO_2$ is 200 GPU. Hollow fiber membranes are used and the selectivity for $CO_2/CH_4$ is higher than 25.

KR20120119755 discloses a method to use low temperature separation method for biogas sourced from food and animal wastes. Raw biogas is stored at 25 C and atmospheric pressure, and is supplied at 1.5 $Nm^3/hr$ and 0.5 bar by a suction pump. $H_2S$ and $NH_3$ are removed by a direct contact of biogas with packing media, and siloxane is adsorbed by activated carbon. Biogas is compressed at medium pressure (~7 bar), and mist filter or dehumidifier removes moisture. Polystyrene hollow fiber membranes separate the purified biogas into $CH_4$ and $CO_2$ (parallel design). Secondary $CH_4$ purification uses ceramic or zeolite-based membranes. The recovered $CO_2$ can be used for industrial purposes or fixation.

CN108624370 is another example of fixation.

U.S. Pat. No. 10,179,883 B2 discloses a system and method of removing $H_2S$ using pressure-temperature swing adsorption (PTSA) and $CO_2$ using two stages of gas separation membranes. The disclosed system is used to upgrade digester biogas containing $O_2$ and high levels of $H_2S$ without additional cost and complexity. The used membranes are selective for $CO_2$ and $O_2$ over $CH_4$.

US20180251694 A1 discloses a method for providing upgraded biogas and a tail gas stream. The biogas upgrading system consists of adsorption, membrane separation, and/or cryogenics. The tail gas enriched with $CO_2$ may be used in medium-BTU equipment due to its combustibility and the upgraded biogas is used for transportation use and/or the generation of fuel credits.

U.S. Pat. No. 9,988,326 B2 discloses a four-stage membrane separation unit to upgrade biogas to biomethane. The third and fourth permeates are discharged from the process and may be used for upgrading $CO_2$ or released to the atmosphere.

US20190030482 A1 discloses a process for recovering methane from digester biogas or landfill gas. Staged membrane modules of at least two different types remove impurities including VOCs, siloxane, $H_2S$, and water from compressed biogas to upgrade biomethane containing at least 94% $CH_4$, below 3% $CO_2$, and below 4 ppm of $H_2S$. The first permeate including $H_2S$, $CO_2$, VOCs, and water is rejected to an output stream for flaring.

CN104003832A discloses a technique and system for simultaneously purifying $CH_4$ and $CO_2$ from marsh gas. The technique comprises a compressor, and two-stage hollow-fiber membrane separation units. Purified $CH_4$ and $CO_2$ satisfy the Vehicle Gas Standard (GB18047-2000) and the Industrial Carbon Dioxide Standard (GB/T6052-2011), respectively.

Known biogas upgrading systems recover $CH_4$ via membrane separation technology and may utilize the separated $CO_2$ source for high purity $CO_2$ liquefaction, industrial-grade $CO_2$ production, chemical fixation, and medium-BTU gas production, or otherwise reject for atmospheric release or flaring. These known practices do not include the recycling of a $CO_2$-rich permeate from a gas separation membrane that is used to recover methane from the raw biogas.

SUMMARY

Given the above-mentioned background, those skilled in the art of biogas production and purification will recognize that there is a need for an integrated production and purification process that does not experience the above-mentioned drawbacks. In particular, there is a need for such a process with improved biological $CH_4$ production and supplemental agitation inside the digester.

There is disclosed a system for improved production of biogas from an anaerobic digester, comprising: an anaerobic digester comprising: i) a tank having a feedstock inlet and a biogas outlet, and ii) a recycle gas injector disposed within the tank adjacent to a bottom thereof, the anaerobic digester being adapted and configured to convert organic feedstock with a culture of anaerobic microbes into a product gas comprising methane and $CO_2$; a feed gas conduit in downstream fluid communication with the anaerobic digester; a gas separation membrane unit comprising one or more gas separation modules in parallel each of which includes a plurality of gas separation membranes that are selective for $CO_2$ over $CH_4$ housed within a pressure vessel having a feed gas inlet in fluid communication with the feed gas conduit, a permeate gas outlet, and a retentate gas outlet, the gas separation membrane unit being adapted and configured to separate a stream of raw biogas obtained from the anaerobic digester into a methane enriched stream of biomethane and a $CO_2$ enriched stream of permeate gas; a product gas conduit adapted and configured to receive the stream of biomethane from the gas separation membrane unit and feed the stream of biomethane towards a point of use; a recycle gas conduit in fluid communication between the permeate gas outlet and the recycle gas injector; and means for providing a driving force comprising a vacuum pump, and/or blower, and/or biogas compressor that is adapted and configured to provide a pressure difference across the plurality of membranes, serving as a driving force for the separation of the stream of raw biogas into the streams of biomethane and permeate gas.

There is also disclosed a method for improved production of biogas from an anaerobic digester. It comprises the following steps. The above-disclosed system is provided. A feedstock having an organic content is fed to the anaerobic digester. The feedstock is converted under anaerobic conditions in the digester into a stream of raw biogas comprising methane and $CO_2$. The stream of raw biogas is separated with the gas separation membrane unit into a biomethane stream comprising at least 60 vol % methane and a permeate gas stream comprising at least 60 vol % $CO_2$. The biomethane stream is fed towards a point of use. The permeate gas stream is recycled back to the digester where the recycled permeate gas stream is injected into digestate contained in the digester. A pressure difference across the plurality of membranes, serving as a driving force separation of the stream of raw biogas into the streams of biomethane and permeate gas, is achieved with the means for providing a driving force.

The system and/or method may include one or more of the following aspects:

the means for providing a driving force comprises a blower that is disposed in the feed gas conduit and configured and which is adapted to boost a pressure of the stream of raw biogas at the feed gas inlet to the membrane.

the means for providing a driving force comprises a vacuum pump that is disposed in the recycle gas conduit and which is configured and adapted to provide a vacuum pressure on the permeate gas outlet.

the means for providing a driving force comprises a biogas compressor that is disposed in the feed gas conduit and which is configured and adapted to boost a pressure of stream of raw biogas at the feed gas inlet.

a point of use receives the biomethane from the product gas conduit, the point of use comprising a compressor that is adapted and configured to compress the biomethane and optionally further purify the compressed biomethane and either inject the compressed biomethane into a pipe of a natural gas grid or into a tank of a compressed natural gas fueled vehicle.

a point of use receives the biomethane from the product gas conduit, the point of use comprising a compressor that is adapted and configured to compress the biomethane and one or more storage vessels for storing the compressed biomethane.

a point of use receiving the biomethane from the product gas conduit, the point of use comprising a generator, other powered equipment, combustor, heater, or boiler consuming the biomethane as fuel gas.

each of the plurality of gas separation membranes is a hollow fiber membrane.

each of the plurality of gas separation membranes is a monolithic asymmetric membrane.

each of the plurality of gas separation membranes is a membrane made of one or more of fluoropolymers, copolymers of polyether-polyamide, polyimides, polysulfones, polycarbonates, cellulosics and polymers of intrinsic morphology (PIMs).

the membranes are made of one or more of fluoropolymers, copolymers of polyether-polyamide, polyimides, or polymers of intrinsic morphology (PIMs) having a $CO_2$/methane selectivity of at least 10 and a $CO_2$ permeance of at least 50 GPU.

each of the plurality of gas separation membranes is a composite hollow fiber membrane comprises a separation layer disposed on a substrate layer, the separation layer is made of one or more of fluoropolymers, copolymers of polyether-polyamide, polyimides, and polymers of intrinsic morphology (PIMs), and the substrate layer is made of one or more of polysulfone, polyvinyledene fluoride, a polyimide, polyether ketone, and polyether ether ketone.

the separation layers are made of one or more of fluoropolymers, copolymers of polyether-polyamide, polyimides, or polymers of intrinsic morphology (PIMs)

having a $CO_2$/methane selectivity of at least 7 and a $CO_2$ permeance of at least 50 GPU.

the separation layers are made of one or more of fluoropolymers, copolymers of polyether-polyamide, polyimides, or polymers of intrinsic morphology (PIMs) having a $CO_2$/methane selectivity of at least 10 and a $CO_2$ permeance of at least 50 GPU.

the means for providing a driving force is controlled to achieve a pressure difference between an exterior and interior of the recycle gas injector so that a recycled stream of permeate gas may be injected by the recycle gas injector into digestate in the digester.

the biomethane stream comprises at least 60 vol % methane.

the permeate gas stream comprises at least 60 vol % $CO_2$.

the digester is operated at a pressure of from 0-2 psig.

operation of the means for providing a driving force is controlled in order to achieve a pressure difference between an exterior and interior of the recycle gas injector so that the stream of permeate gas may be injected into the digestate.

BRIEF DESCRIPTION OF THE DRAWINGS

For a further understanding of the nature and objects of the present invention, reference should be made to the following detailed description, taken in conjunction with the accompanying drawings, in which like elements are given the same or analogous reference numbers and wherein.

DESCRIPTION OF PREFERRED EMBODIMENTS

Figure 1:
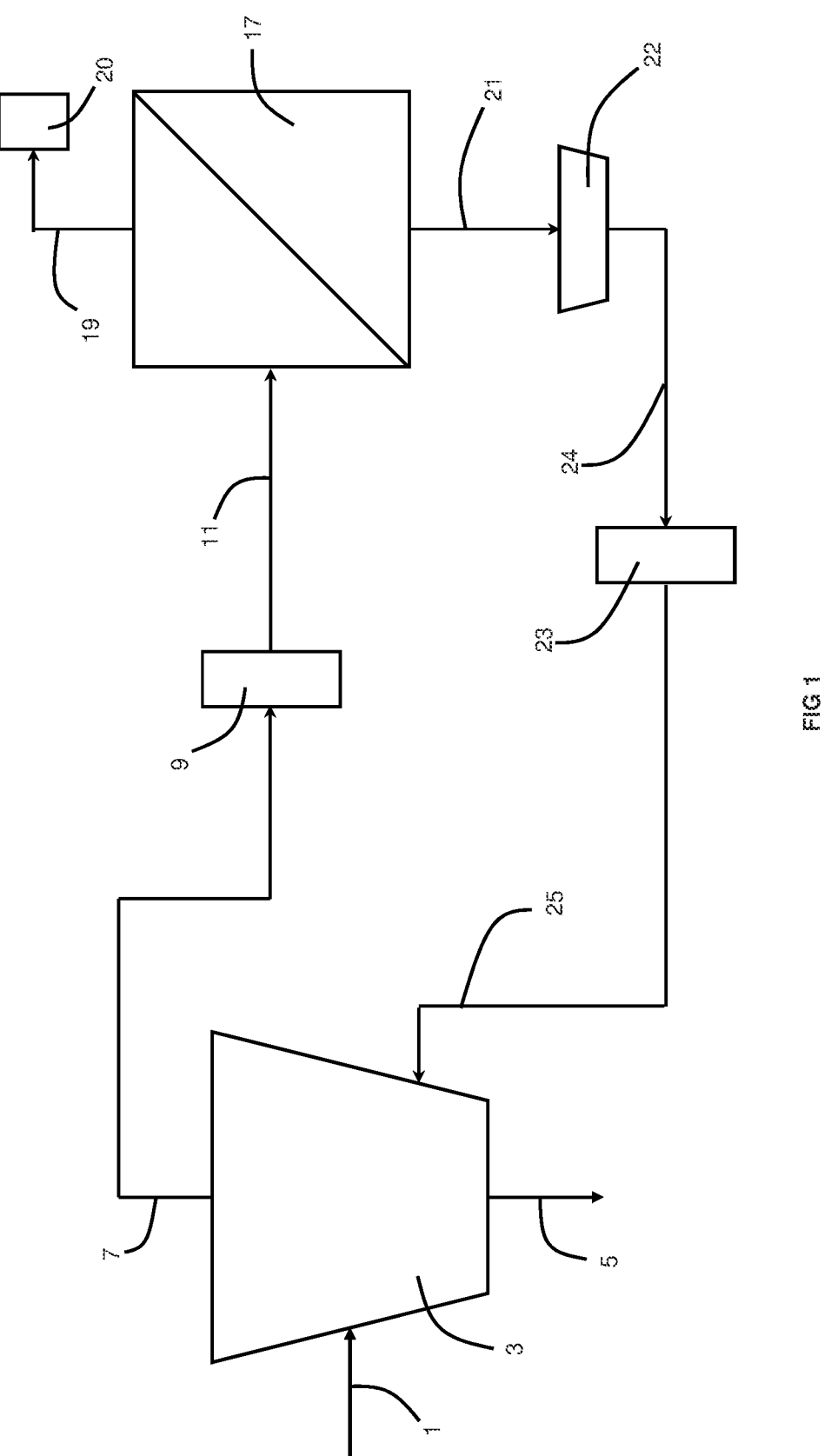
FIG. 1 is a schematic view of an embodiment of the invention including a vacuum pump.

We disclose a synergistic system and process that includes recovery of CH4 from digester gas, produced by an anaerobic digester, through separation of the digester gas at a gas separation membrane unit into a methane enriched retentate gas and also enhanced production of methane in the digester through recycling of a $CO_2$ enriched permeate that is separated from the methane enriched retentate gas by the gas separation membrane unit. In this way, $CO_2$ gas that would otherwise be wholly vented to the atmosphere by the gas separation membrane unit may instead be consumed by microbial cultures in the digester to directly or indirectly produce $CH_4$. In this manner, the $CH_4$ yield of the digester is increased in comparison to conventional schemes. Additionally, the system and process produces decreased amounts of $CO_2$ emissions in comparison to conventional schemes.

The recycled $CO_2$ is converted into $CH_4$ by anaerobic microorganisms in the digester via two microbial pathways—hydrogenotrophic and acetoclastic methanogenesis.

In the hydrogenotrophic methanogenesis, the recycled $CO_2$ is converted directly into $CH_4$ by autotrophic archaea:

$$CO_2 + 4H_2 \rightarrow CH_4 + 2H_2O \quad (1)$$

The recycled $CO_2$ is also converted into acetate by homoacetogenic bacteria according to the following reaction:

$$2CO_2 + 4H_2 \rightarrow CH_3COOH + 2H_2O \quad (2)$$

In the acetoclastic methanogenesis, the produced acetate is converted into $CH_4$ by heterotrophic archaea according to the following reaction:

$$CH_3COOH \rightarrow CH_4 + CO_2 \quad (3)$$

The acetate-associated conversion of $CO_2$ into $CH_4$ is a chain reaction and the overall reaction of reaction (2)+ reaction (3) is the same as the reaction (1). Therefore, the recycled $CO_2$ serves as a carbon source to produce extra $CH_4$, thus improving the $CH_4$ yield.

The digester may be a single tank (i.e., a one-stage digester) in which the entire biogas conversion reaction from hydrolysis to methanogenesis is conducted. Instead, a first tank may serve as the first stage and second tank may serve as the second stage. Regardless of whether the digester is one or two stages, the organic content of the feedstock, such as food or agricultural waste, is metabolized via four consecutive reactions: hydrolysis, acidogenesis, acetogenesis, and methanogenesis.

In a one-stage digester, all intermediate metabolites are consumed by the chain reaction, and $CH_4$ and $CO_2$ are produced as final end products. One-stage digesters include acidogenic bacteria, acetogenic bacteria, and methanogenic archaea.

In a two-stage digester, a single tank may be partitioned? into two stages. In two-stage digesters, the first stage includes acidogenic bacteria that produce acetic acid and is optimized for dark fermentation for production of $H_2$ (i.e., biohydrogen). By utilizing different conditions (such as pH, temperature and hydraulic retention time), one can separate the biological reactions, and separately obtain a hydrogen enriched gas from the first stage and a methane enriched gas from the second stage. Removal of $CO_2$ and $H_2$ from the first stage helps shift the reactions to favor the continuous production of $H_2$. Effluent from the first stage is fed to the second stage. The second stage includes methanogenic archaea that consume $CO_2$ and produce $CO_2$ and $CH_4$ and is optimized for methanogenesis. In the two container scenario, the recycled stream from the membrane unit(s) is introduced to the bottom of the second stage.

The digester tank(s) are typically configured as a cylindrical, rectangular, or egg-shaped tank depending on the purpose of the operation and type of feedstock. The anaerobic microorganisms in the digester may be in suspension or retained on a fixed media carrier. Operation of the digester may be performed in continuous or batch mode. The digestate suspension in the digester may be mixed according to typical techniques such as stirrers and pump. It is also mixed by the action of the rising bubbles resulting from injection of the recycled stream of permeate gas from the gas separation membrane unit. The digester is typically operated at a pressure of 0-2 psig.

The digester is fed with feedstock having a high organic content, such as wastewater solid waste, agricultural waste or food waste. The feedstock is directly injected into the digester or pretreated to increase bioavailability for anaerobic microorganisms. Pretreatment methods include mechanical (e.g., milling, grinding, lysing, high pressure introduction, microwave, ultra-sound, etc), thermochemical (i.e., heating with or without chemicals), or biological (e.g., enzyme or fungal pretreatment) treatment. Complex organic components are first broken down into simple monomers or oligomers including sugars, amino acids, or peptides in the hydrolysis phase. These simple organic components are fermented into H$_2$, CO$_2$, and short-chain fatty acids (e.g., acetate, propionate, butyrate, etc) by acidogenic bacteria. Acetogenic bacteria produce acetate, H$_2$, and CO$_2$ using short-chain fatty acids. Methanogens produce only CH$_4$ using H$_2$ and CO$_2$ (hydrogenotrophic methanogenesis) or produce CH$_4$ and CO$_2$ using acetate (acetoclastic methanogenesis). The feedstock may be drawn from a single source or it may instead be drawn from a cluster of local sources so that a region producing feedstock at a variety of sources at smaller scale may be used to produce biomethane using a single system for production and purification of the biomethane. This may be especially useful for regions which are far from a pipeline of the natural gas grid.

Methane-rich raw biogas (i.e., digester gas) accumulates under the cover of the digester and is removed from its headspace for processing in the gas separation membrane unit.

Before such treatment, it may be fed to a heat exchanger where it exchanges heat with a heat transfer fluid or other process fluid for purposes of heat recovery. Because in the two-stage digester, the first stage reactor is typically maintained under thermophilic conditions of ~50-60 C, the recovered heat may be transferred to the digester with the aforementioned heat transfer fluid technique or the heat may instead by generated by an external source. Bases or acids may be added to the slurry in the digester for purposes of maintaining the alkaline pH of the feedstock for the digester. Additionally, in a two-stage process, a portion of the digestate from the second stage may be recycled back to the first stage to act as a pH buffer.

The gas separation modules and membranes may be configured as flat sheet membranes in a plate and frame style module, flat sheet membranes in a spiral wound style module, or hollow fiber membranes arranged either in parallel to an axis of the gas separation module or spirally wound around a center tube parallel to the axis of the gas separation module. Each of the membranes may be monolithic asymmetric membranes wherein the membranes are made of a single polymeric composition. Alternatively, each of the membranes may be composite membranes having a separation layer made of a first polymeric material disposed on a substrate layer made of a second polymeric material. The polymeric composition of the monolith asymmetric fibers or the separation layer of the composite membranes may include fluoropolymers, copolymers of polyether-polyamide, polyimides, or polymers of intrinsic morphology (PIMs). When present, the polymeric material of the substrate layer may include polysulfone, polyvinyledene fluoride, a polyimide, polyether ketone, or polyether ether ketone. The membranes may be fabricated by any method known in the field of gas separation membranes, including extrusion and coating.

The gas separation membranes produce a methane rich and CO$_2$ deficient retentate gas, in comparison to the raw biogas, comprising at least 60 vol % methane and less than 40 vol % CO$_2$ and a CO$_2$ rich and methane deficient permeate gas, in comparison to the raw biogas, comprising at least 60 vol % CO$_2$ and less than 40 vol % methane. The driving force producing the desired pressure ratio across the membranes is achieved with the use of either a vacuum disposed downstream of the gas separation membrane unit or a blower or compressor disposed upstream of the gas separation membrane unit. A vacuum pump maintains a permeate side membranes at subambient pressure, thereby allowing CO$_2$ to preferentially permeate through the membranes. The thus relatively low pressure stream of permeate gas is delivered from the vacuum pump delivery at a pressure slightly above the pressure of the portion of the digester containing the digestate into which the permeate gas is to be injected. Typically, the stream of permeate gas is delivered from vacuum pump at a relatively higher pressure of 1.0-1.4 bara.

A compressor compresses the stream of raw biogas to a relatively higher pressure of 3-7 bara, yielding a stream of permeate gas (to be injected into the digestate) at a pressure slightly above the pressure of the portion of the digester containing the digestate. For the example, the permeate gas may be at 1-4 psig. Single-stage compressors are commercially available for compressing gases to pressures in the range of 70 psig to 100 psig. For example, a rotary screw compressor or a low pressure single stage reciprocating compressor can be used to compress a gas up to 70 psig. On the other hand, two-stage compressors are generally used for compressing gases to higher pressures in the range of 100 psig to 250 psig. The compressor is a robust and low pressure model; typically a single stage model with a delivery pressure of less than 100 psig. Rotary screw compressors or centrifugal compressors are typically robust enough to be used with minimal gas cleaning.

A blower typically has a maximum pressure ratio of less than 2.5, which may be contrasted with low pressure compressors having a pressure ratio range of about 3-7.

The retentate gas (also known as biomethane) is fed to a point of use where it is either temporarily stored, consumed as fuel gas by a generator or other powered equipment or by a combustor, heater, or boiler, compressed to a higher pressure, additionally purified as needed, and injected into a pipeline of a natural gas grid, or compressed to a higher pressure temporarily stored until being dispensed into a tank of a compressed natural gas fueled vehicle. Additionally, amounts of the biomethane may be combusted in a combustor or boiler where the heat of combustion is transferred to the digester using a heat transfer fluid such as steam.

The permeate gas to be recycled typically comprises at least 60 vol % CO$_2$ and no more than 40 vol % methane. The relatively small recycled stream of permeate gas from the membrane separation unit may optionally be polished to remove contaminants such as H$_2$S, prior to being recycled to the digester, using conventional techniques in order to avoid buildup of such contaminants in the digester. The contaminants may be removed with chemical or physical solvents in an absorptive process. They may be catalytically removed. They may be removed using a non-regenerable adsorbent such as activated carbon. Alternatively, they may be removed in a regenerable adsorbent process using pressure swing adsorption, temperature swing adsorption, pressure temperature swing adsorption, or vacuum swing adsorption. Finally, one need not recycle all of the permeate gas to the digester. For example, the digester might be satisfactorily operated with a desired production of methane while recycling less than the full amount of the permeate to the digester. In another example, some of the permeate may be vented to the atmosphere (with or without further processing) if contaminants (amounts of which are contained in the permeate) start to concentrate in the digester. The portion of permeate gas not recycled to the digester may also be burned in a low BTU combustor to provide heat value to the digester or meet other local needs.

The permeate gas to be recycled typically comprises at least 60 vol % CO$_2$. The recycled stream of permeate may be injected into the digestate at the bottom of the tank using any device known in the field of gas/liquid transfer for transferring a gas into a suspension of solids in water, including a diffuser, a lance, or an eductor. When an eductor is selected, the motive fluid is pumped digestate. The low pressure suction of the accelerated motive fluid causes the recycled permeate gas to be sucked into the ejector where it is mixed with the digestate with the mixture subsequently ejected from the eductor. The recycled permeate gas is injected into the digestate due to a slight pressure difference between the recycled permeate gas in the device and the pressure in the interior of the portion of the digester containing the digestate. Due to this pressure difference, the digestate is mixed to a degree due to the momentum and expansion of the slightly higher recycled permeate gas being injected into the digestate. Additionally, the rising bubbles of injected recycled permeate gas provide another mechanism for achieving mixing of the digestate.

We will now describe embodiments of the invention.

As best illustrated in FIG. 1, a stream of feedstock 1 is fed to an anaerobic digester 3. The feedstock is digested by microbial cultures in the digester 3, producing a stream of excess digestate 5 comprised of low quality solids and a stream of raw biogas 7. The digester 3 is operated at slightly above atmospheric pressure, typically from 0-2 psig.

The stream of excess digestate 5 does not necessarily have to be continuous. Rather, the digestate may be removed in a discontinuous fashion from time to time. For example, the digestate is particularly useful as fertilizer and may be withdrawn when a tanker truck for receiving the digestate is available for a fill. Such tanker trucks will subsequently spread the digestate on agricultural fields as high quality fertilizer. Also, the digestate may be dried and loaded onto trucks for dispersing the solid digestate onto agricultural fields.

In order to avoid damage to the membranes of the gas separation membrane unit 17, the stream of raw biogas 7 may be optionally filtered at filter/coalescing unit 9 in order to remove solid particles and droplets of liquids that may be entrained in the stream of raw biogas 7. The stream of raw biogas 7 (or the stream of filtered raw biogas 11 in the case of the optional filter/coalescing unit 9) is fed to the gas separation membrane unit 17.

The gas separation membrane unit 17 includes one or more gas separation membrane modules in parallel. Each of the gas separation membrane modules includes a pressure vessel having a feed gas inlet, a permeate gas outlet, and a retentate gas outlet. The pressure vessel houses a plurality of gas separation membranes configured as flat sheets or hollow fibers as described above. The membranes are selective for $CO_2$, $H_2$, $H_2O$, $NH_3$, and $H_2S$ over methane. Thus, a relatively greater amount of $CO_2$, $H_2$, $H_2O$, $NH_3$, and $H_2S$ permeates across the membranes and enriches in the permeate gas (that is deficient in methane) while a relatively greater amount of methane is retained on the feed side of the membrane and enriches in the retentate gas (which is deficient in $CO_2$, $H_2$, $H_2O$, $NH_3$, and $H_2S$. Typically, the membranes are selected to have at least a moderately high $CO_2$/methane selectivity of at least 7, typically at least 10, if not a relatively high $CO_2$/methane selectivity of at least 20 Separation of the stream of (filtered) raw biogas 7, 11 is performed with a relatively low pressure difference across the membrane (i.e., the pressure ratio) of only 2-6. The membranes are selected to have at least a moderately high $CO_2$ permeance of 50-150 GPU, if not a relatively high $CO_2$ permeance of greater than 200 GPU. When selecting the membranes, various permutations of moderately high or relatively high selectivity membranes in conjunction with moderately high or relatively high selectivity membranes may be used, depending upon the pressure ratio across the membrane, and therefore, the driving force. Various examples will be discussed below. The gas separation membrane unit 17 produces a stream of retentate gas 19 and a stream of permeate gas 21.

The stream of retentate gas 19 (otherwise known as the stream of biomethane 19) typically contains at least 60 vol % methane, more typically at least 70 vol %. The stream of biomethane 19 is fed to a point of use 20 where it may be temporarily stored, consumed as fuel gas by a generator or other powered equipment or by a combustor, heater, or boiler, compressed to a higher pressure (and optionally further purified before or after compression to remove amounts of contaminants inconsistent with the specifications for compressed natural gas or natural gas pipelines), and injected into a pipeline of a natural gas grid, or compressed to a higher pressure temporarily stored until being dispensed into a tank of a compressed natural gas fueled vehicle. Additionally, amounts of the biomethane may be combusted in a combustor or boiler where the heat of combustion is transferred to the digester using a heat transfer fluid such as steam.

The driving force producing the desired pressure ratio is achieved with the use of a vacuum pump 22. The vacuum pump 22 is adapted and configured to pull a vacuum on the permeate outlets of the pressure vessels of the gas separation membrane modules of the gas separation membrane unit 17. Thus, the pressure ratio (feed/permeate) across the membrane 17 is typically >3.

The higher pressure stream of permeate gas 24 is subsequently optionally polished at treatment unit 23 to remove one or more contaminants using any of the above-mentioned technologies prior to being recycled to the digester 3. With continued reference to FIG. 1, the higher pressure stream of permeate gas 24 (or the optionally polished stream of permeate gas 25) is injected into the digestate in the digester 3 in order to boost production of methane by the associated microbial culture. This is performed with a recycle gas injector (not illustrated) whose open end is submerged in the digestate. The injector may be any device known in the field for injection of gas into a liquid or liquid/solid suspension, including the equipment and techniques explained above. As explained above, due to the pressure difference between the recycled permeate gas inside the injector and the expanded recycled permeate gas just outside an opening of the injector causes the recycled permeate gas to be injected into the digestate. The momentum of the injected gas causes the digestate to be stirred and the bubbles of injected gas rising through the digestate also causes additional stirring.

In this manner, therefore, amounts of $CO_2$ originating from the digester are returned to the digester in precisely the location where they may be used in the most advantageous way: boosting production of methane.

Figure 2:
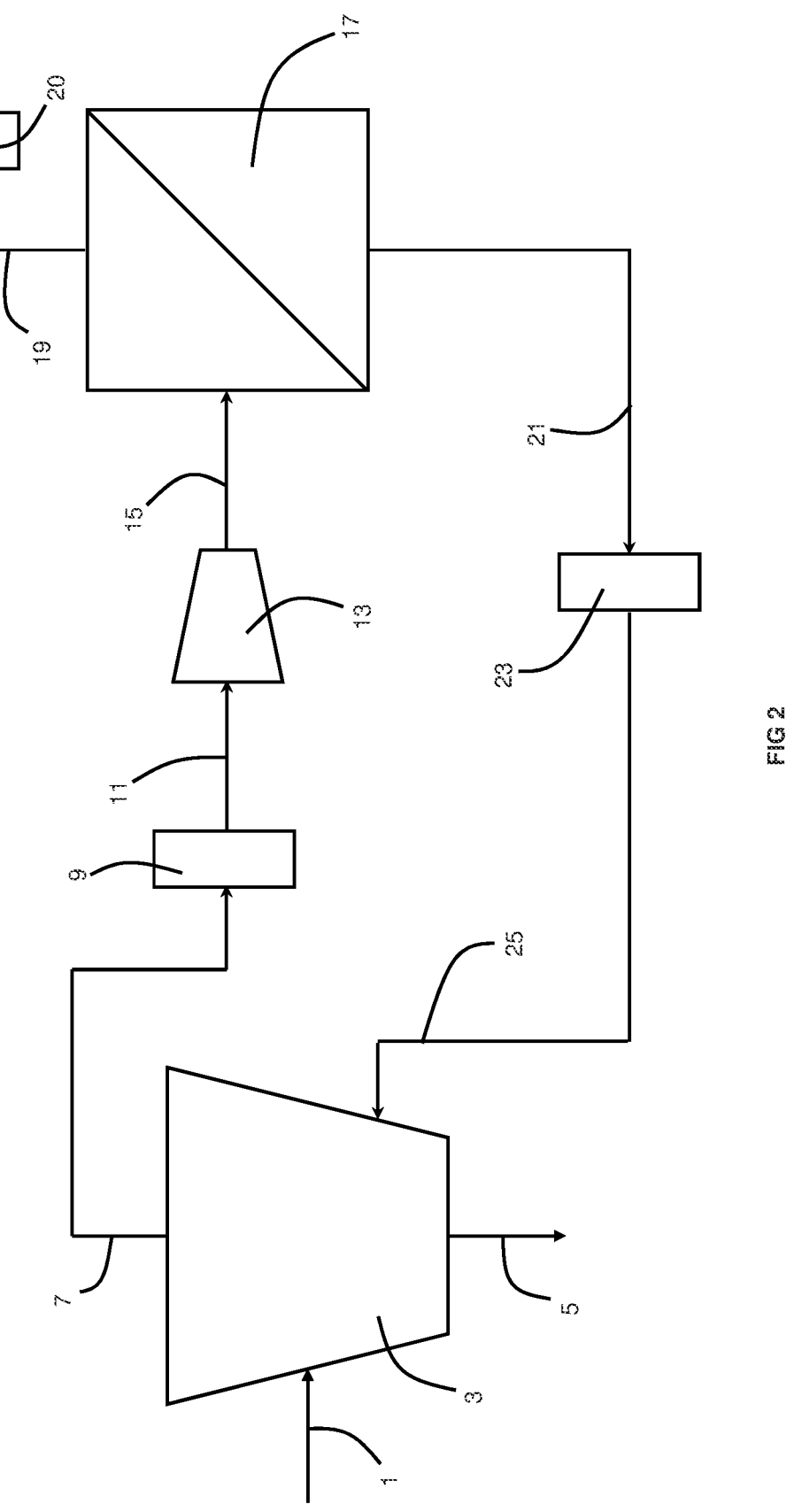
FIG. 2 is a schematic view of an embodiment of the invention including a blower.

As best illustrated in FIG. 2, the stream of raw biogas 7 may also be optionally fed to a filter/coalescing unit 9 where solid particles and fluids entrained in the stream of raw biogas 7 may be removed. In contrast to the vacuum pump embodiment of FIG. 1, the stream of raw biogas 7 (or the stream of filtered raw biogas 11 in the case of the optional filter/coalescing unit 9) is fed to a blower 13 instead of being fed directly to the gas separation membrane unit 17 as is the case of the embodiment of FIG. 1.

The blower 13 raises the pressure of the near-atmospheric pressure stream of raw biogas 7 (or the stream of filtered raw biogas 11 in the case of the optional filter/coalescing unit 9) to a pressure range of 1.5-2.5 bara. This boost in pressure supplies the necessary pressure driving force across the membranes of the gas separation membrane unit 17 because the pressure of the stream of permeate gas 21 to be recycled is only slightly higher than the pressure of the portion of the digester containing the digestate into which the recycled permeate gas is injected. While there is a minor pressure drop resulting from flow of the permeate gas through piping from the gas separation membrane unit 17 to the injector in the digester 3, because the maximum pressure ratio achieved by blowers is generally understood to be 2.5, the pressure ratio across the gas separation membrane unit 17 is up to nearly 2.5.

With continued reference to FIG. 2, the stream of compressed raw biogas 15 is then fed to a gas membrane separation unit 17 that includes one or more gas separation membrane modules in parallel. Each of the gas separation membrane modules includes a pressure vessel having a feed gas inlet, a permeate gas outlet, and a retentate gas outlet. The pressure vessel houses a plurality of gas separation membranes configured as flat sheets or hollow fibers as described above. The membranes are selective for $CO_2$, $H_2$, $H_2O$, $NH_3$, and $H_2S$ over methane. Thus, a relatively greater amount of $CO_2$, $H_2$, $H_2O$, $NH_3$, and $H_2S$ permeates across the membranes and enriches in the permeate gas (which is deficient in methane) while a relatively greater amount of methane is retained on the feed side of the membrane and enriches in the retentate gas (which is deficient in $CO_2$, $H_2$, $H_2O$, $NH_3$ and $H_2S$). Typically, the membranes are selected to have a $CO_2$/methane selectivity of at least 7. Separation of the stream of (filtered) raw biogas 7, 11 is performed with a relatively low pressure difference across the membrane (i.e., the pressure ratio) of less than 2.5. The membranes are selected to have at least a moderately high $CO_2$ permeance of 50-150 GPU, if not a relatively high $CO_2$ permeance of greater than 200 GPU. When selecting the membranes, various permutations of moderately high or relatively high selectivity membranes in conjunction with moderately high or relatively high selectivity membranes may be used, depending upon the pressure ratio across the membrane, and therefore, the driving force. Various examples will be discussed below. The gas separation membrane unit 17 produces a stream of retentate gas 19 and a stream of permeate gas 21.

The stream of retentate gas 19 rich (otherwise known as a stream of biomethane 19 typically contains at least 60 vol %, more typically at least 70 vol %. The stream of biomethane 19 is fed to a point of use 20 where it may be temporarily stored, consumed as fuel gas by a generator or other powered equipment or by a combustor, heater, or boiler, compressed to a higher pressure (and optionally further purified before or after compression as discussed above), and injected into a pipeline of a natural gas grid, or compressed to a higher pressure temporarily stored until being dispensed into a tank of a compressed natural gas fueled vehicle. Additionally, amounts of the biomethane may be combusted in a combustor or boiler where the heat of combustion is transferred to the digester using a heat transfer fluid such as steam.

The stream of permeate gas 25 is subsequently optionally polished at treatment unit 23 to remove one or more contaminants using any of the above-mentioned technologies prior to being recycled to the digester 3

With continued reference to FIG. 2, the stream of permeate gas 21 (or optionally polished stream of permeate gas 25) is injected into the digestate in the digester 3 in order to boost production of methane by the associated microbial culture. This is performed with a recycle gas injector (not illustrated) whose open end is submerged in the digestate. The injector may be any device known in the field for injection of gas into a liquid or liquid/solid suspension, including the equipment and techniques explained above. As explained above, due to the pressure difference between the recycled permeate gas inside the injector and the expanded recycled permeate gas just outside an opening of the injector causes the recycled permeate gas to be injected into the digestate. The momentum of the injected gas causes the digestate to be stirred and the bubbles of injected gas rising through the digestate also causes additional stirring.

In this manner, therefore, amounts of $CO_2$ originating from the digester are returned to the digester in precisely the location where they may be used in the most advantageous way: boosting production of methane.

Figure 3:
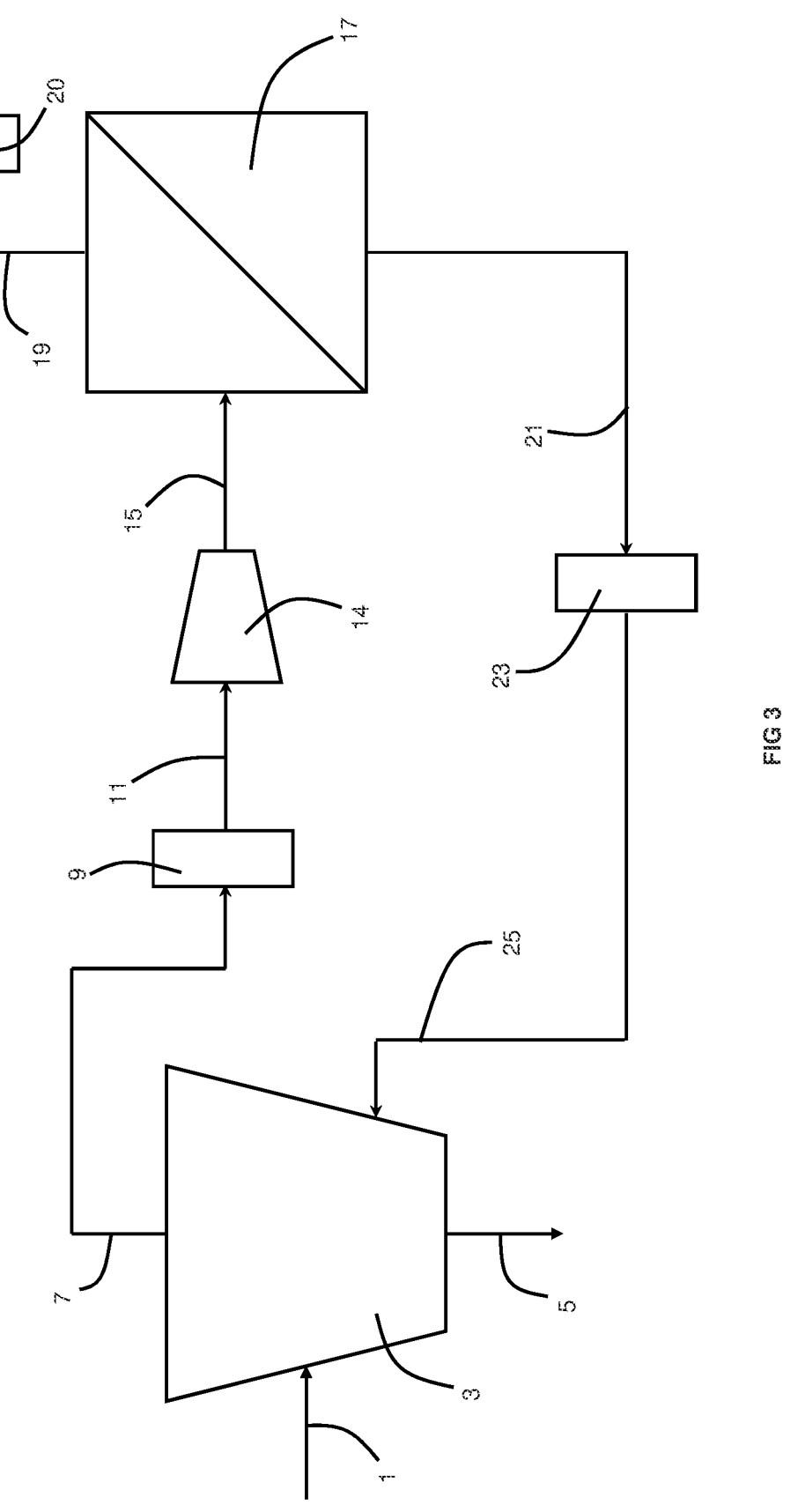
FIG. 3 is a schematic view of an embodiment of the invention including a compressor.

The embodiment of FIG. 3 is the same as for FIG. 2 with some notable exceptions.

First, instead of using a blower to boost a pressure of the stream of raw biogas 7 or the stream of filtered raw biogas 11 in the case of the optional filter/coalescing unit 9) a compressor 14 is used to compress the stream of raw biogas 7 or the stream of filtered raw biogas 11 in the case of the optional filter/coalescing unit 9) to a pressure range from 3-7 bara. Depending upon the pressure desired for the stream of compressed raw biogas 15 and the pressure ratio of the particular compressor employed, one or more stages of compression may be used to reach the desired pressure.

Second and in comparison to the embodiments of FIGS. 1-2, separation of the stream of (filtered) raw biogas 7, 11 in the embodiment of FIG. 3 is performed with a relatively high pressure difference across the membrane (i.e., the pressure ratio) from 3 to as much as 7. The membranes are selected to have at least a moderately high $CO_2$ permeance of 50-150 GPU, if not a relatively high $CO_2$ permeance of greater than 200 GPU. When selecting the membranes, while various permutations of moderately high or relatively high selectivity membranes in conjunction with moderately high or relatively high selectivity membranes may be used (depending upon the pressure ratio across the membrane, and therefore, the driving force), typically the membranes have a moderately high selectivity membrane of greater than 7, typically greater than 10, in combination with a relatively high permeance of at least 50 GPU.

While each of the embodiments of FIGS. 1-3 are quite satisfactory, each of them is particular suitable for particular points of use for the biomethane. For example, use of a vacuum pump or low pressure blower, whose maximum pressure ratio is limited, is particularly suitable when the produced biomethane is to be used in low pressure applications such as combustion. On the other hand, use of a higher pressure compressor is particularly suitable when the produced biomethane is to be further compressed and further purified for injection into a pipeline of a natural gas grid or for filling the tanks of compressed natural gas fueled vehicles.

EXAMPLES

Example 1: Scheme 1 (Vacuum Permeate) with Moderate Permeance/High Selectivity Membrane With reference to the system of FIG. 1, this scheme operates the anaerobic digester process to provide a 15-20 psia raw biogas feed to the membrane and uses a vacuum pump with 75% adiabatic efficiency to provide 2-6 psia on the permeate side.

This example shows a simulation of the process using membranes having a relatively high $CO_2$/methane selectivity of 40 and moderate $CO_2$ permeance of 80 GPU. The membrane is a hollow fiber device with 165 micron OD hollow fibers that exhibits a $CO_2$ permeance of 80 GPU and a methane permeance of only 2 GPU. The temperature and pressure conditions of the feed gas (of raw biogas) are 30 C° and 20 psia. The pressure of the stream of permeate gas 21 is 4 psia. Stream 21 is recompressed by the vacuum pump 22, which is operated at a 75% adiabatic efficiency back to a pressure of 20 psia prior to recycle back to the digester. The process simulation results in a stream of biomethane 19 with ~80% methane and less than 20% $CO_2$). Various properties exhibited by the simulation are listed in Table 1 below.

TABLE 1

| | | Process parameters for Example 1 | | | | |
|---|---|---|---|---|---|---|
| Feed | Retentate | | Permeate | | Vacuum pump power | Membrane area |
| nm³/h | nm³/h | % $CO_2$ | nm³/h | % $CO_2$ | kW | m² |
| 100 | 52.7 | 19.8 | 47.3 | 83.5 | 3.7 | 1714 |

Figure 4:
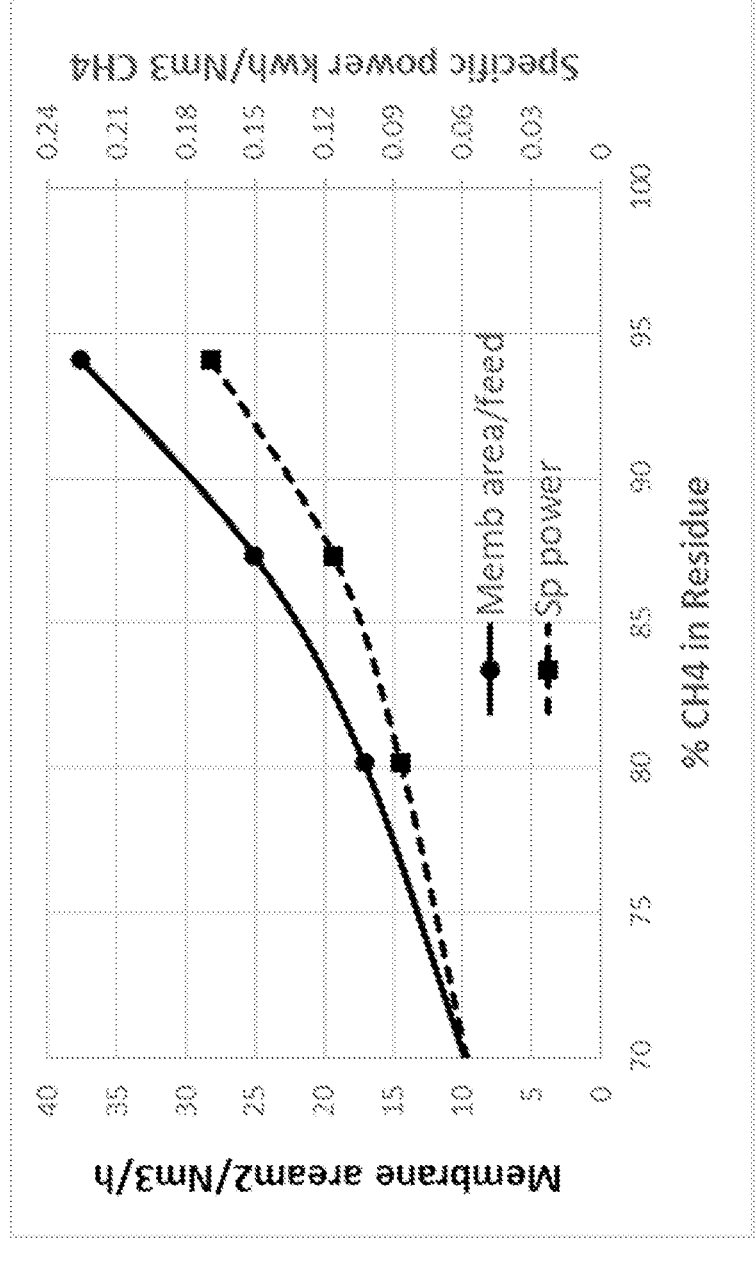
FIG. 4 is a graph of specific membrane area and specific power vs % CH4 in the residue (retentate) for Example 1.

The membrane stage cut, defined as the ratio of permeate/feed flows, can be varied for a given feed and constant pressure/temperature parameters by changing the membrane area. Alternatively, for a fixed membrane area and operating parameters, the feed flow can be varied in order to change the membrane stage cut. The effect of the membrane stage cut upon the $CO_2$ content in the stream of biomethane 19 was further modelled. The required specific membrane area and specific power requirements at varying methane product purity are shown in FIG. 4. A 90% methane concentration in the stream of biomethane 19 would require a specific membrane area of 25 m² per nm³/h of raw biogas fed to the gas separation membrane unit 17 and a specific power (for the vacuum pump 22) of 0.15 kW per nm³/h of methane in the stream of biomethane gas 19. The membrane/process configuration of this Example requires a relatively high membrane area but minimizes the energy cost of separation.

Example 2: Scheme 1 (Vacuum Permeate) Using a Membrane with a High $CO_2$ Permeance and a Moderate $CO_2$/Methane Selectivity This Example uses the same scheme as used in Example 1 except that the membrane has a lower $CO_2$/methane selectivity of 20 but a higher $CO_2$ permeance of 800 GPU. Also, the membrane is a hollow fiber device with 350 micron OD fibers having a $CO_2$ permeance of 800 GPU and a methane permeance of 40 GPU. The process simulation results in a stream of biomethane 19 with 80% methane and less than 20% $CO_2$. Various properties exhibited by the the simulation are listed in Table 2 below.

TABLE 2

| | | process parameters for Example 2 | | | | |
|---|---|---|---|---|---|---|
| Feed | Retentate | | Permeate | | Vacuum pump power | Membrane area |
| nm³/h | nm³/h | % $CO_2$ | nm³/h | % $CO_2$ | kW | m² |
| 100 | 43.4 | 19.3 | 56.6 | 73.5 | 4.4 | 179 |

Figure 5:
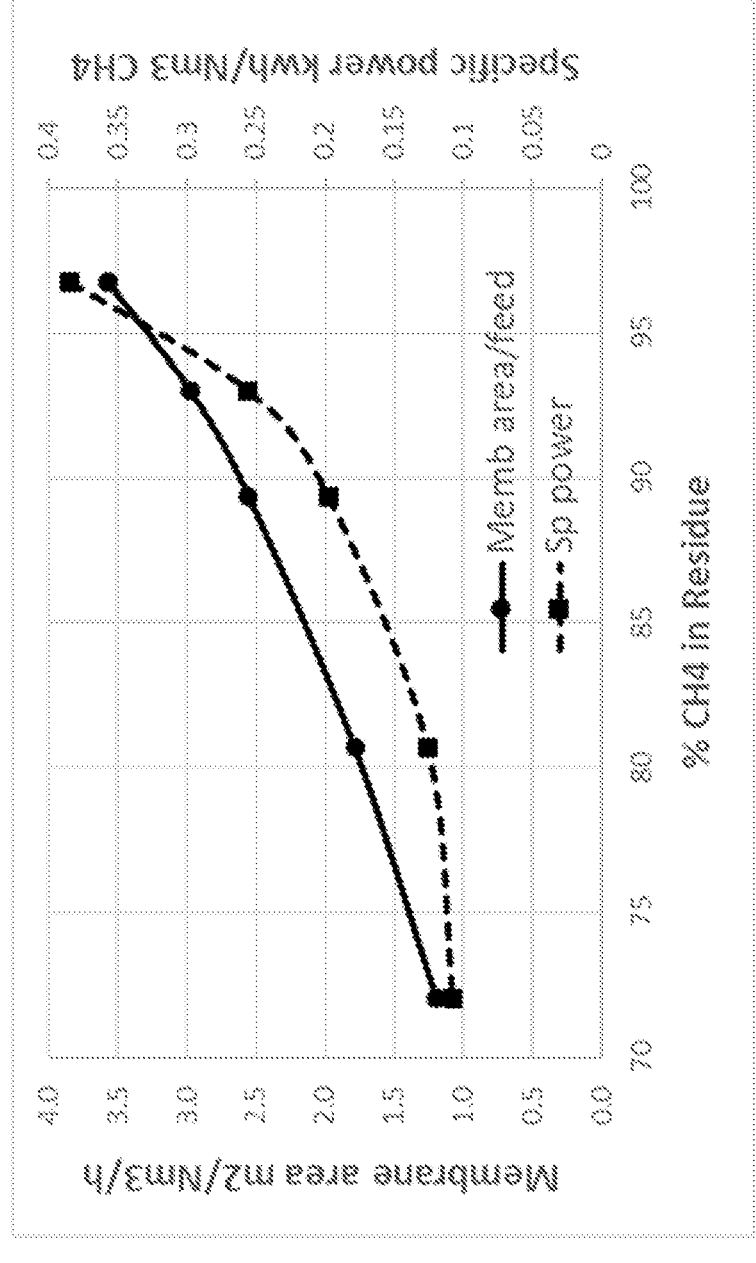
FIG. 5 is a graph of specific membrane area and specific power vs % CH4 in the residue (retentate) for Example 2.

The effect of the membrane stage cut upon the $CO_2$ content in the stream of biomethane 19 was further modelled. The required specific membrane area and specific power requirements at varying methane product purity are shown in FIG. 5. A 90% methane purity in the stream of biomethane 19 would require 2.6 m² per nm³/h of raw biogas fed to the gas separation membrane unit 19 and a specific power (for the vacuum pump 22) of 0.2 kW per nm³/h of methane in the stream of biomethane 19. The membrane/process configuration of this Example minimizes membrane area requirement with a modest increase (compared to Example 1) in the energy cost of separation.

Example 3: Scheme 2 (2× Feed Compression) Using a Membrane with a High $CO_2$ Permeance and a Moderate $CO_2$/Methane Selectivity This scheme (based upon the system of FIG. 2) uses a single stage compression device to provide a moderate 2× pressure increase for the raw biogas gas (a 50:50 mixture of $CO_2$ and methane) fed to the membrane. In this scheme, the anaerobic digester process operates at 15 psia. A blower with a 75% adiabatic efficiency is used to provide a 30 psia biogas feed to the membrane while the permeate gas is at 15 psia. The membrane permeate is fed to the bottom of the anaerobic digester.

The membrane is a hollow fiber device with 350 micron OD hollow fibers having a $CO_2$ permeance of 800 GPU and a methane permeance of 40 GPU. A process simulation case results in a stream of biomethane 19 with ~80% methane and less than 20% $CO_2$. Various properties exhibited by the simulation are listed in Table 3 below.

TABLE 3

| | | process parameters | | | | |
|---|---|---|---|---|---|---|
| Feed | Retentate | | Permeate | | Blower power | Membrane area |
| nm³/h | nm³/h | % $CO_2$ | nm³/h | % $CO_2$ | kW | m² |
| 100 | 26.1 | 19.1 | 73.9 | 60.9 | 3.0 | 298 |

Figure 6:
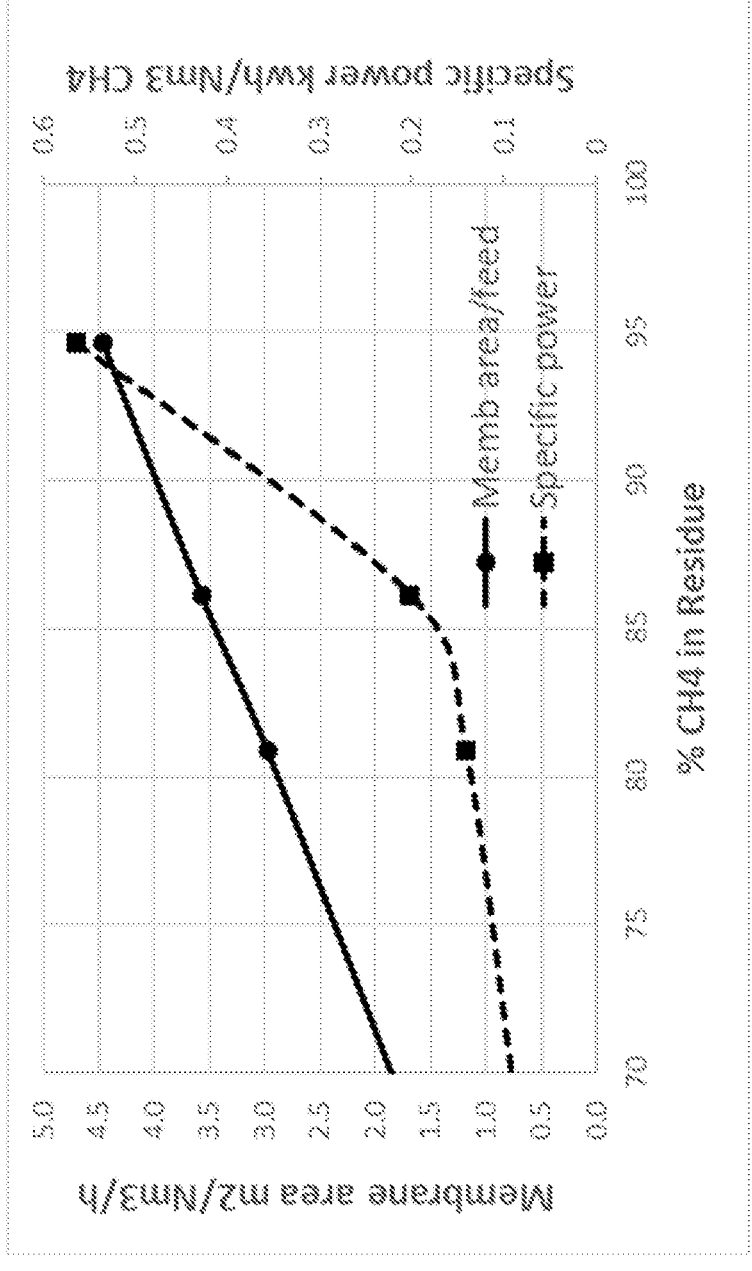
FIG. 6 is a graph of specific membrane area and specific power vs % CH4 in the residue (retentate) for Example 3.

The effect of the membrane stage cut upon the $CO_2$ content in the stream of biomethane 19 was further modelled. The required specific membrane area and specific power requirements at varying methane product purity are shown in FIG. 6. As seen in FIG. 6, this pressure/selectivity scheme is not optimal for achieving a methane purity in the stream of biomethane of greater than 85%. A 85% methane purity in the stream of biomethane 19 would require 3.5 m² per nm³/h of raw biogas fed to the gas separation membrane unit 17 and a specific power (for the blower) of 0.18 kW per nm³/h of methane in the stream of biomethane 19. The membrane/process configuration of this Example is simple to operate, has attractive membrane area and energy cost requirements but is not suitable for higher methane product purities. It would be highly suitable when the biomethane 19 is used as a fuel gas locally.

Example 4: Scheme 2 (4× Feed Compression) Using a Membrane with a High $CO_2$ Permeance and Moderate $CO_2$/Methane Selectivity This scheme (based upon the system of FIG. 3) uses a single stage compression device to provide a moderate 4× pressure increase for the feed gas. In this scheme, the anaerobic digester process operates at 15 psia. A blower with a 75% adiabatic efficiency is used to provide a 60 psia pressure raw biogas (a 50:50 mixture of $CO_2$ and methane) for feeding to the membrane while the permeate side is at 15 psia. The membrane permeate is fed to the bottom of the anaerobic digester.

The membrane is a hollow fiber device with 350 micron OD fibers having a $CO_2$ permeance of 800 GPU and a methane permeance of 40 GPU, yielding a $CO_2$/methane selectivity of 20. Two different process simulation cases were completed to produce a stream of biomethane 19 with ~80% methane and less than 20% $CO_2$ and with ~90% methane and less than 10% $CO_2$. Various properties exhibited by the simulation are listed in Table 4 below.

TABLE 4

| process parameters for Example 4 | | | | | | |
|---|---|---|---|---|---|---|
| Feed | Residue | | Permeate | | Specific power Kwh/nm³ CH₄ in | Specific Membrane area m²/nm³/h |
| nm³/h | nm³/h | % CO₂ | nm³/h | % CO₂ | product | feed |
| 100 | 47.9 | 19.9 | 52.1 | 77.7 | 0.18 | 0.45 |
| 100 | 33.5 | 10.0 | 66.5 | 70.2 | 0.23 | 0.71 |

The membrane/process configuration of this Example requires higher compression costs but minimizes the membrane area required for higher purity product.

The invention provides several advantages.

The integrated system and method are cost-effective process and exhibit improve biomethane production yield by producing raw biogas, separating the $CO_2$ from the raw biogas to provide biomethane, and recycling $CO_2$-enriched permeate to the same anaerobic digestion reactor that produced the raw biogas.

The disclosed system and method have a relatively lower capital expense associated with construction of the facility and equipment because they are well suitable for converting the organic content of feedstock collected from a "cluster" of sources to allow a single installation for production of biomethane for the region having the cluster of sources.

Because the system and method can scale up biomethane production from a cluster of sources, it more easily justifies the building of a pipeline to the system from natural gas grid.

Compared to conventional high pressure biogas upgrading processes with the ultimate aim to prepare a product biogas that can meet high purity spec such as for pipeline or compressed natural gas (CNG), the disclosed biogas separation and recirculation system presents the following advantages of:

Allowing a lower energy-intensive biogas upgrading process via a low pressure membrane purification process using relatively high $CO_2$ permeance (such as 50-150 GPU) membranes without requiring a compressor so as to produce biomethane that could be used locally for heating as a conventional fuel gas or that could be further upgraded to compressed & purified product biomethane with higher quality specifications.

Improving the methane yield of raw biogas produced by the anaerobic digester through recirculation of the $CO_2$-enriched permeate to the anaerobic digestion reactor in order to enhance the bioactivity of methane producing microorganisms (e.g., hydrogenotrophic/acetoclastic methanogens).

Improving mixing of the digestate with injection of the recycled permeate gas.

Compared to previous biogas upgrading processes, in some embodiments of the system and method, the membrane separation process of this system and method operates at substantially the same pressure as the digester. There is negligible feed gas compression, other than possibly a blower. Conventional membrane-based biogas upgrading processes operate at much higher pressures than the digester.

In the embodiment of Example 1, using a vacuum pump and membranes with moderately high $CO_2$ permeance, and relatively high $CO_2$/$CH_4$ selectivity, product gas at only a moderate purity (e.g., up to 95 vol % $CH_4$ in product) may be produced for local use as an upgraded fuel gas source, or compressed to a pressure allowing its use as compressed natural gas (CNG) in, for example, CNG fueled vehicles, or even upgraded to natural gas pipeline quality, either individually, or combined with the purified biomethane from other digesters in the local area. The embodiment of Example 1 uses relatively simple mechanical equipment: a vacuum pump.

The embodiment of Example 2, using a vacuum pump and membranes with moderately high $CO_2$/$CH_4$ selectivity, and relatively high $CO_2$ permeance, exhibits advantages similar to those of Example 1. Because the membranes of Example 2 have a higher $CO_2$ permeance, the gas separation membrane unit may use a smaller overall membrane surface area in comparison to Example 1. At the same time, in comparison to Example 1, this is associated with a higher energy cost associated with the vacuum pump.

In the embodiment of Example 3 using a blower and membranes with moderately high $CO_2$/$CH_4$ selectivity and relatively high $CO_2$ permeance, product gas at only a moderate purity (e.g., up to 85-95 vol % $CH_4$ in product) may be produced for local use as an upgraded fuel gas source, for compression to CNG, or for upgrading to natural gas pipeline quality, either individually or combined with biomethane from other digesters in the local area. The embodiment of Example 1 uses relatively simple mechanical equipment: a blower. When lower product gas purities of only 85 vol % methane are needed, the embodiment of Example 3 provides a very economical solution.

Regardless of whether a vacuum pump, blower, or compressor at low power is used, the membrane-based separation of the raw biogas may be performed using a single membrane stage. Current commercial membrane-based biogas upgrading systems utilize two or even three membrane stages, requiring a significantly higher pressure in the raw biogas fed to the first stage. In contrast to such commercial systems, the membranes of the gas separation membrane unit of the invention requires relatively little driving force: only a blower, a vacuum pump, or a relatively low pressure compressor. The purification correspondingly consumes little energy as well, about 0.2 kwh per $nm^3$ of CH4 in the enriched product gas.

Because the membrane separation process of the invention is simple to operate, it may be installed economically on relatively smaller digesters such as those operating on wastewater waste, food waste, or agricultural waste feedstock.

Membrane treatment of raw biogas from an anaerobic digesters treating animal waste from a herd of ~1,000 cows uses significant pretreatment. $H_2S$ and organics are removed by PSA and activated carbon with potentially even more polishing needed after the membrane step. Such anaerobic digesters operate at higher pressures of ~10 bar because the end product is usually a pipeline. In contrast to systems receiving raw biogas from such anaerobic digesters, the system of the present invention is meant to be a lower capital expense system for handling animal waste from a herd of only 100-150 cows with minimal pretreatment. Digesters receiving such an amount of animal waste are operated at lower pressures. This means that the product gas, which is enhanced in heating value, but does not have the high purities typically produced by more robust membrane systems (receiving the high flow rate of biogas produced by anaerobic digesters treating the waste of 1,000 cows), can be economically used in generation of heat/electricity on site. The system of the present invention thus typically produces product gas flow rates of around 0.1-10 $nm^3/h$ or 0.1-100 $nm^3/h$.

While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims. The present invention may suitably comprise, consist or consist essentially of the elements disclosed and may be practiced in the absence of an element not disclosed. Furthermore, if there is language referring to order, such as first and second, it should be understood in an exemplary sense and not in a limiting sense. For example, it can be recognized by those skilled in the art that certain steps can be combined into a single step.

The singular forms "a", "an" and "the" include plural referents, unless the context clearly dictates otherwise.

"Comprising" in a claim is an open transitional term which means the subsequently identified claim elements are a nonexclusive listing i.e. anything else may be additionally included and remain within the scope of "comprising." "Comprising" is defined herein as necessarily encompassing the more limited transitional terms "consisting essentially of" and "consisting of"; "comprising" may therefore be replaced by "consisting essentially of" or "consisting of" and remain within the expressly defined scope of "comprising".

"Providing" in a claim is defined to mean furnishing, supplying, making available, or preparing something. The step may be performed by any actor in the absence of express language in the claim to the contrary.

Optional or optionally means that the subsequently described event or circumstances may or may not occur. The description includes instances where the event or circumstance occurs and instances where it does not occur.

Ranges may be expressed herein as from about one particular value, and/or to about another particular value. When such a range is expressed, it is to be understood that another embodiment is from the one particular value and/or to the other particular value, along with all combinations within said range.

All references identified herein are each hereby incorporated by reference into this application in their entireties, as well as for the specific information for which each is cited.

What is claimed is:

1. A system for improved production of biogas from an anaerobic digester, comprising:

an anaerobic digester comprising:

i) a tank having a feedstock inlet and a biogas outlet, and ii) a recycle gas injector disposed within the tank adjacent to a bottom thereof, the anaerobic digester being adapted and configured to convert organic feedstock with a culture of anaerobic microbes into a product gas comprising methane and $CO_2$;

a feed gas conduit in downstream fluid communication with the anaerobic digester;

a gas separation membrane unit comprising one or more gas separation modules each of which includes a plurality of gas separation membranes that are selective for $CO_2$ over $CH_4$ housed within a pressure vessel having a feed gas inlet in fluid communication with the feed gas conduit, a permeate gas outlet, and a retentate gas outlet, the gas separation membrane unit being adapted and configured to separate a stream of raw biogas obtained from the anaerobic digester into a methane enriched stream of biomethane and a $CO_2$ enriched stream of permeate gas;

a product gas conduit adapted and configured to receive the stream of biomethane from the gas separation membrane unit and feed the stream of biomethane towards a point of use;

a recycle gas conduit in fluid communication between the permeate gas outlet and the recycle gas injector; and means for providing a driving force comprising a vacuum pump, blower, and/or biogas compressor that is adapted and configured to provide a pressure difference across the plurality of membranes serving as a driving force for the separation of the stream of raw biogas into the streams of biomethane and permeate gas.

2. The system of claim 1, wherein the means for providing a driving force comprises a blower that is disposed in the feed gas conduit and configured and which is adapted to boost a pressure of the stream of raw biogas at the feed gas inlet.

3. The system of claim 1, wherein the means for providing a driving force comprises a vacuum pump that is disposed in the recycle gas conduit and which is configured and adapted to provide a vacuum pressure on the permeate gas outlet.

4. The system of claim 1, wherein the means for providing a driving force comprises a biogas compressor that is disposed in the feed gas conduit and which is configured and adapted to boost a pressure of stream of raw biogas at the feed gas inlet.

5. The system of claim 1, further comprising a point of use receiving the biomethane from the product gas conduit, the point of use comprising a compressor that is adapted and configured to compress the biomethane and optionally further purify the compressed biomethane and either inject the compressed biomethane into a pipe of a natural gas grid or into a tank of a compressed natural gas fueled vehicle.

6. The system of claim 1, further comprising a point of use receiving the biomethane from the product gas conduit, the point of use comprising a compressor that is adapted and configured to compress the biomethane and one or more storage vessels for storing the compressed biomethane.

7. The system of claim 1, further comprising a point of use receiving the biomethane from the product gas conduit, the point of use comprising a generator, other powered equipment, combustor, heater, or boiler consuming the biomethane as fuel gas.

8. The system of claim 1, wherein each of the plurality of gas separation membranes is a hollow fiber membrane made of one or more of fluoropolymers, copolymers of polyether-polyamide, polyimides, and polymers of intrinsic morphology (PIMs).

9. The system of claim 8, wherein the hollow fiber membranes are made of one or more of fluoropolymers, copolymers of polyether-polyamide, polyimides, or polymers of intrinsic morphology (PIMs) having a $CO_2$/methane selectivity of at least 10 and a $CO_2$ permeance of at least 50 GPU.

10. The system of claim 1, wherein each of the plurality of gas separation membranes is a composite hollow fiber membrane comprising a separation layer disposed on a substrate layer, the separation layer being made of one or more of fluoropolymers, copolymers of polyether-polyamide, polyimides, and polymers of intrinsic morphology (PIMs), the substrate layer being made of one or more of polysulfone, polyvinyledene fluoride, a polyimide, polyether ketone, and polyether ether ketone.

11. The system of claim 10, wherein the separation layers are made of one or more of fluoropolymers, copolymers of polyether-polyamide, polyimides, or polymers of intrinsic morphology (PIMs) having a $CO_2$/methane selectivity of at least 7 and a $CO_2$ permeance of at least 50 GPU.

12. The system of claim 10, wherein the $CO_2$/methane selectivity is at least 10.

13. The system of claim 1, wherein the means for providing a driving force is controlled to achieve a pressure difference between an exterior and interior of the recycle gas injector so that a recycled stream of permeate gas may be injected by the recycle gas injector into digestate in the digester.

14. A method for improved production of biogas from an anaerobic digester, comprising the steps of:

providing the system of claim 1;

feeding a feedstock having an organic content to the anaerobic digester;

converting the feedstock under anaerobic conditions in the digester into a stream of raw biogas comprising methane and $CO_2$;

separating the stream of raw biogas with the gas separation membrane unit into a biomethane stream comprising at least 60 vol % methane and a permeate gas stream comprising at least 60 vol % $CO_2$;

feeding the biomethane stream towards a point of use; and recycling the permeate gas stream back to the digester where the recycled permeate gas stream is injected into digestate contained in the digester, wherein a pressure difference across the plurality of membranes, serving as a driving force separation of the stream of raw biogas into the streams of biomethane and permeate gas, is achieved with the means for providing a driving force.

15. The method of claim 14, wherein the biomethane stream comprises at least 60 vol % methane.

16. The method of claim 14, wherein the digester is operated at a pressure of 0-2 psig.

17. The method of claim 14, wherein operation of the means for providing a driving force is controlled in order to achieve a pressure difference between an exterior and interior of the recycle gas injector so that the stream of permeate gas may be injected into the digestate.

\* \* \* \* \*